United States Patent
Stewart et al.

(10) Patent No.: US 11,021,724 B2
(45) Date of Patent: Jun. 1, 2021

(54) MATERIALS AND METHODS FOR ALKENE REDUCTION OF LEVOGLUCOSENONE BY AN ALKENE REDUCTASE

(71) Applicants: University of Florida Research Foundation, Inc., Gainesville, FL (US); AgroParisTech, Paris (FR)

(72) Inventors: Jon Dale Stewart, Orlando, FL (US); Florent Allais, Bouy (FR); Louis Michel Marie Mouterde, Reims (FR)

(73) Assignees: University of Florida Research Foundation, Inc., Gainsville, FL (US); AfroParisTech, Paris (FR)

( * ) Notice: Subject to any disclaimer, the term of this patent is extended or adjusted under 35 U.S.C. 154(b) by 0 days.

(21) Appl. No.: 16/490,556

(22) PCT Filed: Mar. 29, 2018

(86) PCT No.: PCT/US2018/025184
§ 371 (c)(1),
(2) Date: Sep. 1, 2019

(87) PCT Pub. No.: WO2018/183706
PCT Pub. Date: Oct. 4, 2018

(65) Prior Publication Data
US 2020/0010865 A1    Jan. 9, 2020

Related U.S. Application Data

(60) Provisional application No. 62/478,430, filed on Mar. 29, 2017.

(51) Int. Cl.
*C12P 17/18* (2006.01)

(52) U.S. Cl.
CPC ..... *C12P 17/181* (2013.01); *C12Y 106/99001* (2013.01)

(58) Field of Classification Search
CPC . C12P 17/18; C12P 17/181; C12Y 106/99001
See application file for complete search history.

(56) References Cited

U.S. PATENT DOCUMENTS

| | | | |
|---|---|---|---|
| 4,994,585 A | 2/1991 | Koseki et al. | |
| 5,112,994 A | 5/1992 | Koseki et al. | |
| 6,046,043 A * | 4/2000 | Murthy | C07D 487/04 435/129 |

FOREIGN PATENT DOCUMENTS

WO    2015-165957 A1    11/2015

OTHER PUBLICATIONS

Amato et al., Applications of protein engineering to members of the old yellow enzyme family. Biotechnol. Advances., 2015, vol. 33: 624-631. (Year: 2015).*
Banerjee et al., Improving enzymes for bionass conversion: A basic research perspective. Bioenerg. Res., 2010, vol. 3: 82-92. (Year: 2010).*
Brige et al., Comparative characterization and expression analysis of the four old yellow enzyme homologues from Shewanella oneidensis indicate differences in physiological function. Biochem. J., 2006, vol. 394: 335-344. (Year: 2006).*
Chica et al., Semi-rational approaches to engineering enzyme activity: combining the benefits of directed evolution and rational design. Curr. Opi. Biotechnol., 2005, vol. 16: 378-384. (Year: 2005).*
Pompeu et al., Structural and catalytic characterization of Pichia stipitis OYE 2.6, a useful biocatalyst for asymmetric alkene reductions. Adv. Synth. Catal., 2012, vol. 354: 1949-1960 (Year: 2012).*
Sen et al., Developments in directed evolution for enzyme functions. Appl. Biochem. Biotechnol., 2007, vol. 143: 212-223. (Year: 2007).*
Stott et al., Old yellow enzyme. The J. Biol. Chem., 1993, vol. 268(9): 6097-6106. (Year: 1993).*
Whisstocketal., Prediction of protein function from protein sequence. Q. Rev. Biophysics., 2003, vol. 36 (3): 307-340. (Year: 2003).*
Turrini et al., Enzymatic synthesis of optically active lactones via asymmetric bioreduction using ene-reductases from old yellow enzyme family. Adv. Synth. Catal., 2015, vol. 357: 1861-1871. (Year: 2015).*
Cao et al., Dehydration of cellulose to levoglucosenone using polar aprotic solvents. Energy Environ. Sci., 2015, vol. 8: 1808-1815. (Year: 2015).*
Krishna et al., Hydrogenation of levoglucosenone to renewable chemicals. Green Chem., 2017, vol. 19: 1278-1285. (Year: 2017).*

(Continued)

*Primary Examiner* — Ganapathirama Raghu
(74) *Attorney, Agent, or Firm* — Thomas | Horstemeyer, LLP

(57) ABSTRACT

The subject invention concerns materials and methods for alkene reduction of compounds, such as levoglucosenone (LGO) and (S)-γ-hydroxymethyl-α,β-butenolide (HBO), using an alkene reductase enzyme. In one embodiment, a method of the invention comprises alkene reduction of a target compound by reacting the compound with an Old Yellow Enzyme (OYE) that reduces alkene bonds. In one embodiment, the OYE is OYE 2.6 from *Pichia stipites* and comprises the amino acid sequence of SEQ ID NO: I. In a specific embodiment, the enzyme is an Old Yellow Enzyme (OYE) 2.6 mutant having an amino acid substitution at position 78 in the sequence, wherein the tyrosine at position 78 is substituted with a tryptophan amino acid (Y78W) and is designated as OYE 2.6 Y78W (SEQ ID NO:2).

16 Claims, 6 Drawing Sheets
Specification includes a Sequence Listing.

(56) References Cited

OTHER PUBLICATIONS

Patterson-Orazem et al., Pichia stipitis OYE 2.6 variants with improved catalytic efficiencies from site-saturation mutagenesis libraries. Bioorg. Med. Chem., 2014, vol. 22: 5628-5632. (Year: 2014).*
Sherwood et al., Dihydrolevoglucosenone (Cyrene) as bio-based alternative for dipolar aprotic solvents. Chem. Commun., 2014, vol. 50: 9650-9652. (Year: 2014).*
International Search Report in co-pending, related PCT Application PCT/US2018/025184, dated Jul. 24, 2018.
Flourat, et al. "Chemo-Enzymatic Synthesis of Key Intermediates (s)-gamma-hydroxymethyl-alpha, bet a-but enolide and (s)-gamma-hydroxymethyl-gamma-butyrolactone via Lipase-mediated Baeyer-Villiger Oxidation of Levoglucosenone", Green Chemistry, 2015, vol. 17, pp. 404-412.
Walton, Adam, et al., "Residues Controlling Racial Selectivity in an Alkene Reductase and Semirational Alterations to Create Sterocomplementary Variants", ACS Catalysis, 2014, vol. 4, pp. 2307-2318.
Mouterde, et al., "Enzymatic Reduction of Levoglucoseone by an Alkene Reductase (OYE 2.6): a sustainable metal- and dihydrogen-free access to the bio-based solvent Cyrene", Green Chem, 2018, vol. 20, pp. 5528-5532.
Extended European search report of Application No. 18777109.2 dated Jan. 11, 2021.
Walton Adam Z; Stewart Jon D: "Chapter 13: Applications of Saccharomyces pastorianus Old Yellow Enzyme to asymmetric alkene reductions" In: Hille R; Miller S; Palfey B: "Handbook of Flavoproteins: Complex Flavoproteins, Jehydrogenases and Physical Methods", De Gruyter, Berlin, Boston, XP009524655, ISBN: 9783110298345 vol. 22013, pp. 299-320.
Erica D. Amato et al: "Applications of protein engineering to members of the old yellow enzyme family", BIOTECHNOLOGY Advances., vol. 33, No. 5, Sep. 1, 2015 (Sep. 1, 2015), pp. 624-631, XP055761001.
Florian Diot-Neant et al: "Sustainable Synthesis and Polycondensation of Levoglucosenone-Cyrene-Based Bicyclic Dial Monomer: Access to Renewable Polyesters", CH Emsusch EM, vol. 13, No. 10, May 15, 2020 [(May 15, 2020), pp. 2613-2620.

* cited by examiner

MATERIALS AND METHODS FOR ALKENE REDUCTION OF LEVOGLUCOSENONE BY AN ALKENE REDUCTASE

CROSS REFERENCE TO RELATED APPLICATIONS

This application is the 35 U.S.C. § 371 national stage application of PCT Application No. PCT/US2018/025184, filed Mar. 29, 2018, which application claims the benefit of U.S. Provisional Application Ser. No. 62/478,430, filed Mar. 29, 2017, both of which are hereby incorporated by reference herein in their entireties, including any figures, tables, nucleic acid sequence, amino acid sequences, or drawings.

GOVERNMENT SUPPORT

This invention was made with government support under 1111791 awarded by the National Science Foundation. The government has certain rights in the invention.

BACKGROUND OF THE INVENTION

Alkene reductase enzymes have become increasingly popular biocatalysts for converting prochiral substrates into optically pure building blocks [1-14]. Flavoproteins of the Old Yellow Enzyme superfamily are particularly useful for this purpose and a variety of homologs have been studied since the seminal work by Massey on *Saccharomyces pastorianus* OYE 1 [15,16]. These enzymes require no metal ions for catalytic activity and the reductions can be conducted under aqueous conditions.

Levoglucosenone (LGO) is a chiral platform chemical that can be produced from the catalytic fast pyrolysis of cellulose (see U.S. Publication No. 2012/0111714). LGO has the structure:

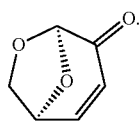

(LGO)

A variety of molecules can be synthesized from LGO, and from the alkene reduction product, 2,3-dihydro-levoglucosenone (2H-LGO), which is a molecule with a high added value (e.g., green solvent). 2,3-dihydro-levoglucosenone has value, for example, as a dipolar aprotic solvent.

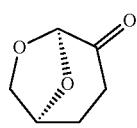

(2H-LGO)

It is possible to reduce the double bond of LGO by a classic reduction using Pd/C under $H_2$ atmosphere; however, this process is not generally considered "green chemistry" since it requires organic solvents and the introduction of heavy metal ions in the reaction which must later be removed. Thus, there remains a need in the art for an enzymatic pathway to try to overcome this issue.

BRIEF SUMMARY OF THE INVENTION

The subject invention concerns materials and methods for alkene reduction of compounds, such as levoglucosenone (LGO) and (S)-γ-hydroxymethyl-α,β-butenolide (HBO), using an alkene reductase enzyme. In one embodiment, a method of the invention comprises alkene reduction of a target compound by reacting the compound with an Old Yellow Enzyme (OYE) that reduces alkene bonds. In specific embodiments, LGO is contacted with an OYE to produce 2,3-dihydro-levoglucosenone (2H-LGO). In one embodiment, the OYE is OYE 2.6 from *Pichia sapitis* (GenBank Accession Nos. 3UPW_A and 3TJL_A) and comprises the amino acid sequence of SEQ ID NO:1. In a specific embodiment, the enzyme is an Old Yellow Enzyme (OYE) 2.6 mutant having an amino acid substitution at position 78 in the sequence, wherein the tyrosine at position 78 is substituted with a tryptophan amino acid (Y78W) and is designated as OYE 2.6 Y78W (SEQ ID NO:2).

BRIEF DESCRIPTION OF THE DRAWINGS

FIGS. 1B-1 and 1B-2 show GC/MS spectrum of 2,3-dihydro-levoglucosenone/Continuous extraction.

FIG. 2 shows $^1$H NMR spectrum of 2,3-dihydro-levoglucosenone (2H-LGO).

BRIEF DESCRIPTION OF THE SEQUENCES

Figures 1, 1A:
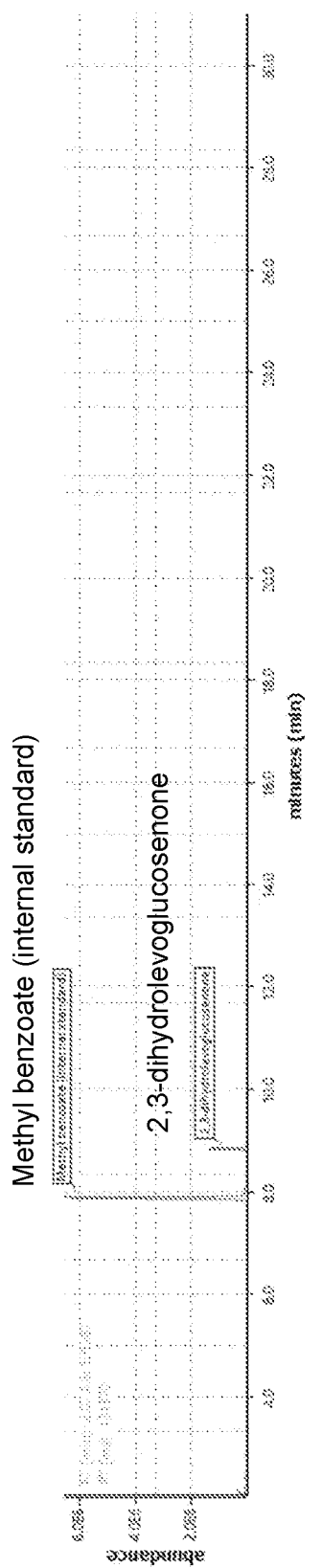
FIGS. 1A-1 and 1A-2 show GC/MS spectrum of 2,3-dihydro-levoglucosenone/Quick extraction.

SEQ ID NO:1 is an amino acid sequence of Old Yellow Enzyme 2.6.

SEQ ID NO:2 is an amino acid sequence of Old Yellow Enzyme 2.6 Y78W.

DETAILED DESCRIPTION OF THE INVENTION

The subject invention concerns materials and methods for alkene reduction of compounds, such as levoglucosenone (LGO), using an alkene reductase enzyme. The methods of the invention can be used to cleanly and efficiently produce chemicals, drugs, herbicides, surfactants, etc. In one embodiment, a method of the invention comprises alkene reduction of a target compound by reacting the compound with an Old Yellow Enzyme (OYE), or an enzymatically active fragment or variant thereof, that reduces alkene bonds. In some embodiments, the OYE is from *Saccharomyces* (such as *S. pastorianus*, *S. cerevisiae*, and *S. carlsbergensis*) or *Pichia*. In specific embodiments of the methods, LGO is contacted with an OYE to produce 2,3-dihydro-levoglucosenone (2H-LGO). In a specific embodiment, the OYE is OYE 2.6 from *Pichia stipitis* (GenBank Accession Nos. 3UPW_A and 3TJL_A) and comprises the amino acid sequence of SEQ ID NO:1, or an enzymatically active fragment or variant thereof. In one embodiment, the enzyme is an OYE mutant having an amino acid substitution at position 78 in the sequence. In a more specific embodiment, the enzyme is an OYE 2.6 mutant having an amino acid substitution at position 78 in the sequence, wherein the tyrosine at position 78 is substituted with a tryptophan amino acid (Y78W) and is designated as OYE 2.6 Y78W (SEQ ID NO:2), or an enzymatically active fragment or variant thereof.

In one embodiment of the methods, levoglucosenone is contacted with an effective amount of OYE 2.6 Y78W in a suitable solvent, such as an aqueous solvent. The LGO can be dissolved in an alcohol, such as ethanol. In a specific embodiment, an LGO solution is added dropwise to the reaction mixture over the course of several hours. In an exemplified embodiment, the LGO solution is added dropwise to the reaction mixture over about six hours. In specific embodiments, the reaction mixture can comprise one or more of glucose, potassium phosphate, NADP+ and glucose dehydrogenase. The reaction can be allowed to proceed for a suitable period of time, e.g., several hours. Completion of the reaction can be performed by testing for the presence/amount of LGO remaining in the reaction mixture. The alkene reduction product can be extracted from the solution following reaction completion using, for example, ethyl acetate and evaporation of the organic phase. The methods of the invention can also be used for alkene reduction of other molecules, such as (S)-γ-hydroxymethyl-α,β-butenolide (HBO).

Methods of the present invention allow for the preparation of desired molecules through a safer (no organic solvent nor hydrogen needed), greener (no harmful reagents) and less toxic (no residual metal) synthetic process. This is particularly useful in the case of fine chemicals or end products used in the pharmaceutic, cosmetic and food/feed sectors. Moreover, compared to commonly used metal-catalyzed hydrogenation of levoglucosenone, the methods of the present invention provide better yield and do not require a purification step to remove a Pd catalyst.

Substitution of amino acids other than those specifically exemplified or naturally present in a wild type or mutant enzyme of the invention are also contemplated within the scope of the present invention. For example, non-natural amino acids can be substituted for the amino acids of a polypeptide, so long as the polypeptide having the substituted amino acids retains substantially the same biological or functional activity (e.g., enzymatic) as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form. Allelic variants of a protein sequence of a wild type enzyme of the present invention are also encompassed within the scope of the invention.

Amino acids can be generally categorized in the following classes: non-polar, uncharged polar, basic, and acidic. Conservative substitutions whereby an enzyme of the present invention having an amino acid of one class is replaced with another amino acid of the same class fall within the scope of the subject invention so long as the polypeptide having the substitution still retains substantially the same biological or functional activity (e.g., enzymatic) as the polypeptide that does not have the substitution. Table 1 provides a listing of examples of amino acids belonging to each class.

TABLE 1

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

Fragments and variants of an enzyme are contemplated within the scope of the present invention and can be generated and tested for the presence of enzymatic function using standard techniques known in the art. Thus, an ordinarily skilled artisan can readily prepare and test fragments and variants of an enzyme of the invention and determine whether the fragment or variant retains enzymatic activity relative to full-length or a non-variant enzyme.

Enzymes contemplated within the scope of the subject invention can also be defined in terms of more particular identity and/or similarity ranges with those sequences of the invention specifically exemplified herein or known in the art. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% as compared to a sequence exemplified herein. Unless otherwise specified, as used herein percent sequence identity and/or similarity of two sequences can be determined using the algorithm of Karlin and Altschul [21], modified as in Karlin and Altschul [22]. Such an algorithm is incorporated into the NBLAST and XBLAST programs of Altschul et al. [19]. BLAST searches can be performed with the NBLAST program, score=100, wordlength=12, to obtain sequences with the desired percent sequence identity. To obtain gapped alignments for comparison purposes, Gapped BLAST can be used as described in Altschul et al. [20]. When utilizing BLAST and Gapped BLAST programs, the default parameters of the respective programs (NBLAST and)(BLAST) can be used. See NCBI/NIH website.

Single letter amino acid abbreviations are defined in Table 2.

TABLE 2

| Letter Symbol | Amino Acid |
| --- | --- |
| A | Alanine |
| B | Asparagine or aspartic acid |
| C | Cysteine |
| D | Aspartic Acid |
| E | Glutamic Acid |
| F | Phenylalanine |
| G | Glycine |
| H | Histidine |
| I | Isoleucine |
| K | Lysine |
| L | Leucine |
| M | Methionine |
| N | Asparagine |
| P | Proline |

TABLE 2-continued

| Letter Symbol | Amino Acid |
|---|---|
| Q | Glutamine |
| R | Arginine |
| S | Serine |
| T | Threonine |
| V | Valine |
| W | Tryptophan |
| Y | Tyrosine |
| Z | Glutamine or glutamic acid |

Materials and Methods 2,3-dihydro-levoglucosenone (2H-LGO). To a reaction mixture containing 200 mM glucose, 100 mM $KP_i$, pH 7.5 and 0.3 mM nicotinamide adenine dinucleotide phosphate ($NADP^+$) in a final volume of 50 mL, was added 125 Units of glucose dehydrogenase (GDH, Codexis CDX-901) and 375 µg of purified Y78W Old Yellow Enzyme 2.6 (Y78W OYE 2.6). The solution was gently stirred at room temperature and 120 µL (1 mmol) of levoglucosenone (LGO) dissolved in 1.5 mL of ethanol was added dropwise over 6 hours, reaching a final concentration of 20 mM. Completion of the reaction was verified by removing 500 µL of the reaction mixture, adding 500 µL of ethyl acetate+0.01% methyl benzoate, and vortex mixing for 30 seconds. The organic phase was analyzed by GC-MS using a 0.25 mm×30 m DB-17 column. No GC peak corresponding to LGO was observed, indicating that the reaction was complete. The 50 mL reaction mixture was subjected to continuous extraction with 75 mL of ethyl acetate overnight, then the organic phase was evaporated under vacuum to give pure 2H-LGO with ~99% conversion and in quantitative yield.

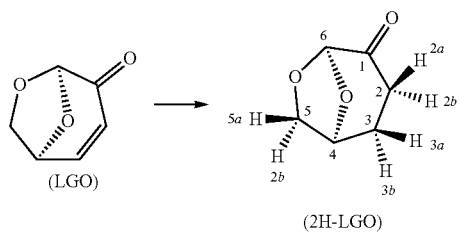

GC-MS: m/z 128 (2.6%), 100 (52%), 82 (40%), 70 (23%), 57 (37%), 54 (100%) (see FIGS. 1A-1, 1A-2, 1B-1, and 1B-2).

Figures 1, 1A, 2:
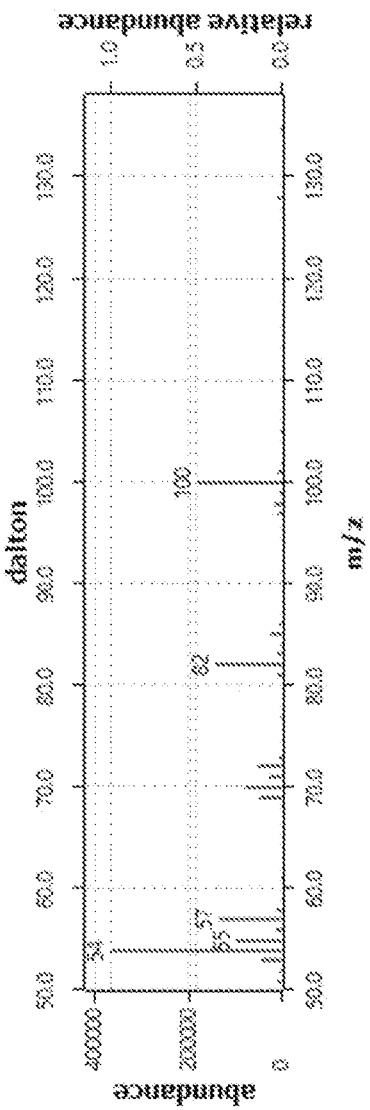
Figures 1, 1B, 2:
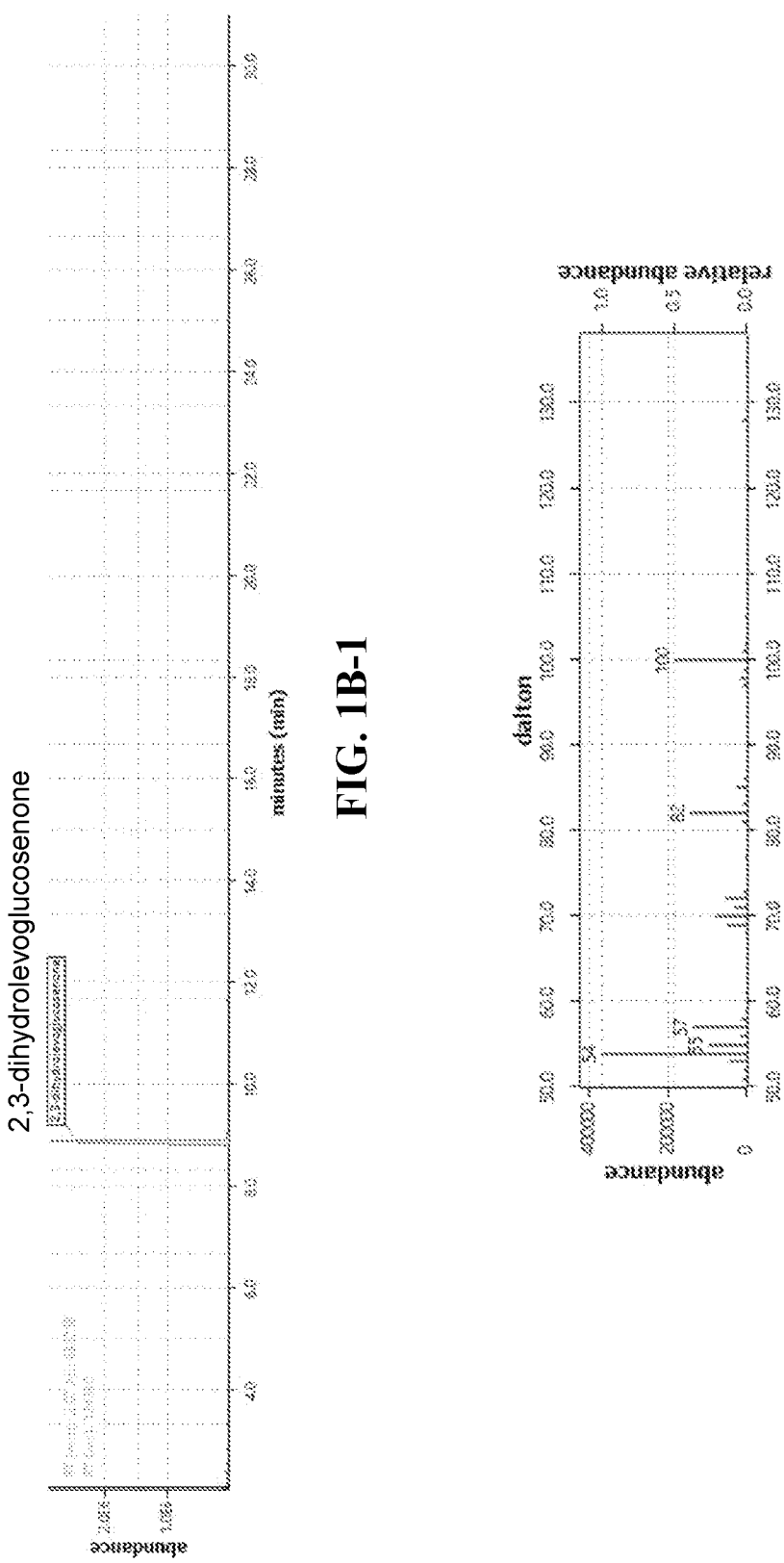
Figure 2:
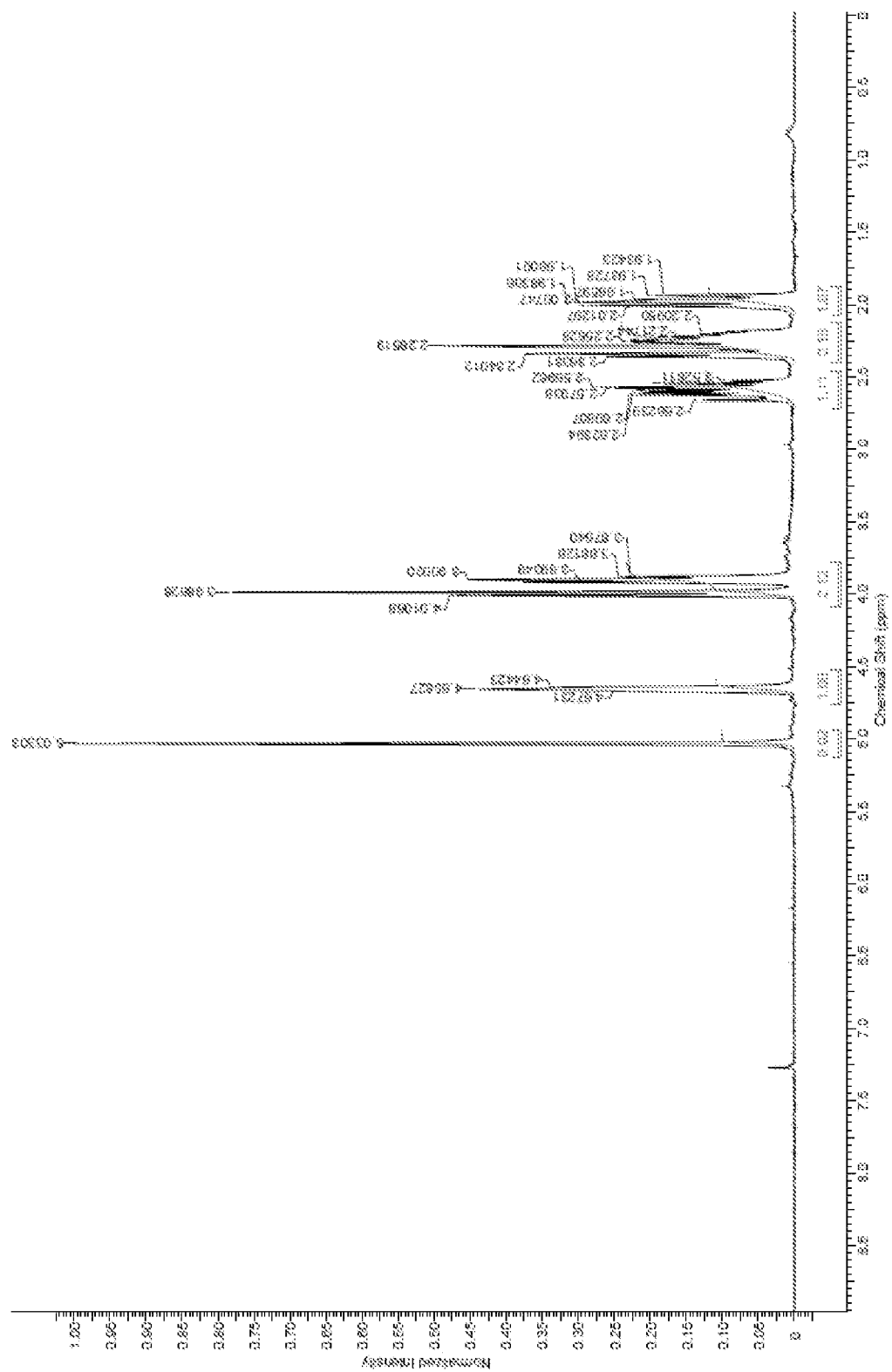

$^1$H NMR (300 MHz, $CDCl_3$): δ 5.03 (s, 1H, $H_6$), 4.66 (m, $1H_{5b}$), 3.98 (m, 2H, $H_{5a,4}$), 2.58 (m, 1H, $H_{2a}$), 2.28 (m, 2H, $H_{2b,3a}$), 2.00 (m, 1H, $H_{3b}$) (see FIG. 2).

Figure 3:
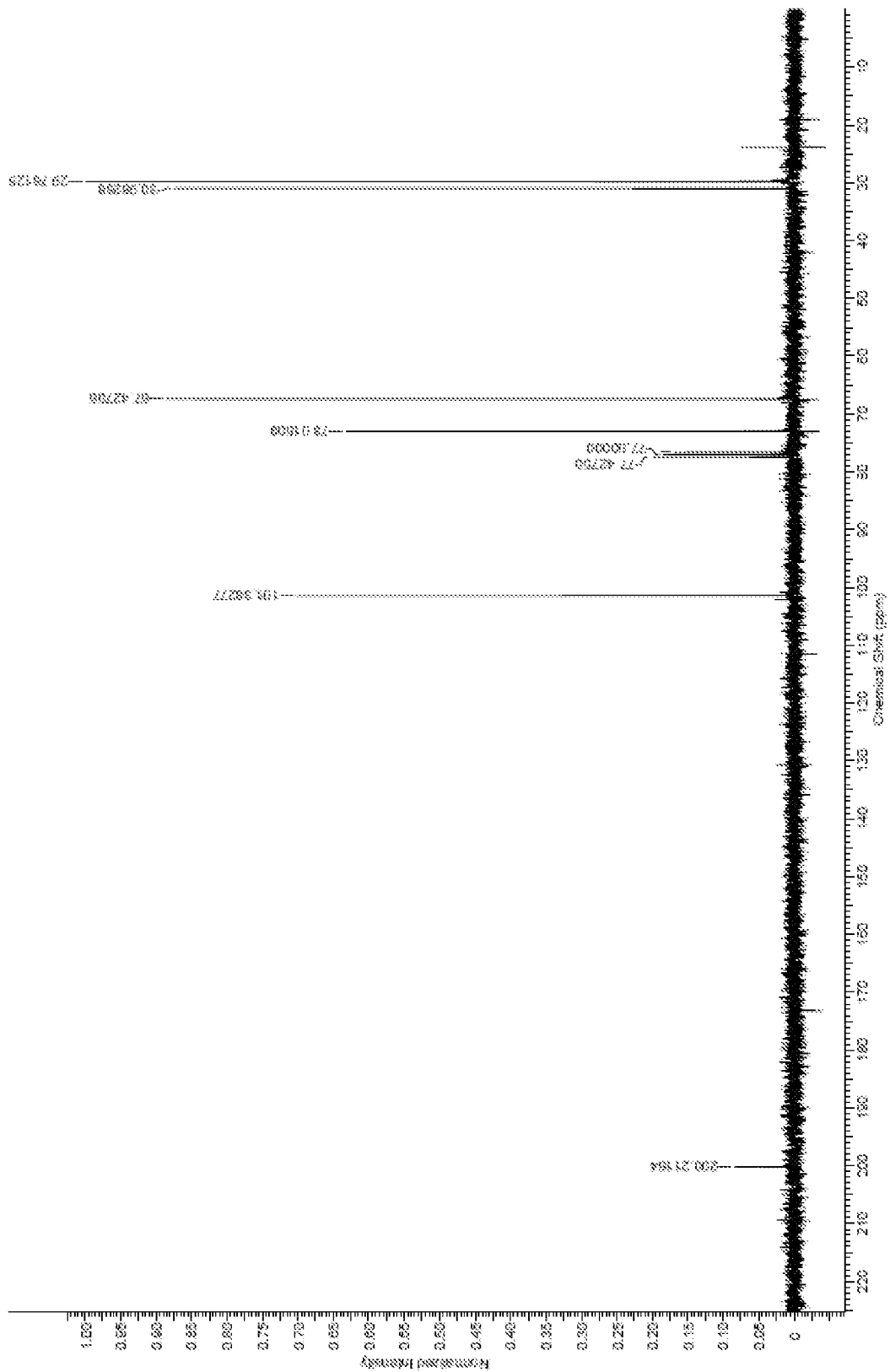
FIG. 3 shows $^{13}$C NMR spectrum of 2,3-dihydro-levoglucosenone (2H-LGO).

$^{13}$C NMR (100 MHz, $CDCl_3$): δ 200.2 (s, $C_1$), 101.4 (d, $C_6$), 73.0 (d, $C_4$), 67.4 (t, $C_5$), 31.0 (t, $C_2$), 29.8 (t, $C_3$) (see FIG. 3).

(S)-γ-hydroxymethyl-α,β-butyrolactone (2H-HBO). To a reaction mixture containing 50 mM $KP_i$, pH 7.5, and 10 mM NADPH, with a final volume of 1 mL, was added 75 µg of Y78W OYE 2.6 and 10 mM (1.20 µL, mmol) of (S)-γ-hydroxymethyl-α,β-butenolide (HBO). The reaction mixture was stirred at room temperature overnight, and then evaporated using a Speed-Vac. The resulting crude oil was then dissolved in $D_2O$ and analyzed by $^1$H NMR. The absence of the peaks corresponding to the alkene bond suggest that the reaction went to completion. A control reaction with all components except Y78W OYE 2.6 gave no evidence of reduction by $^1$H NMR.

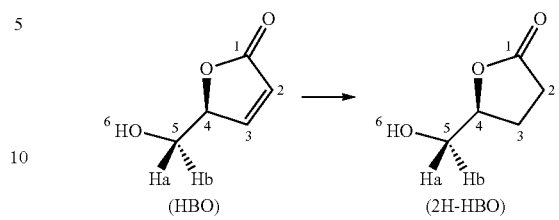

Figure 4:
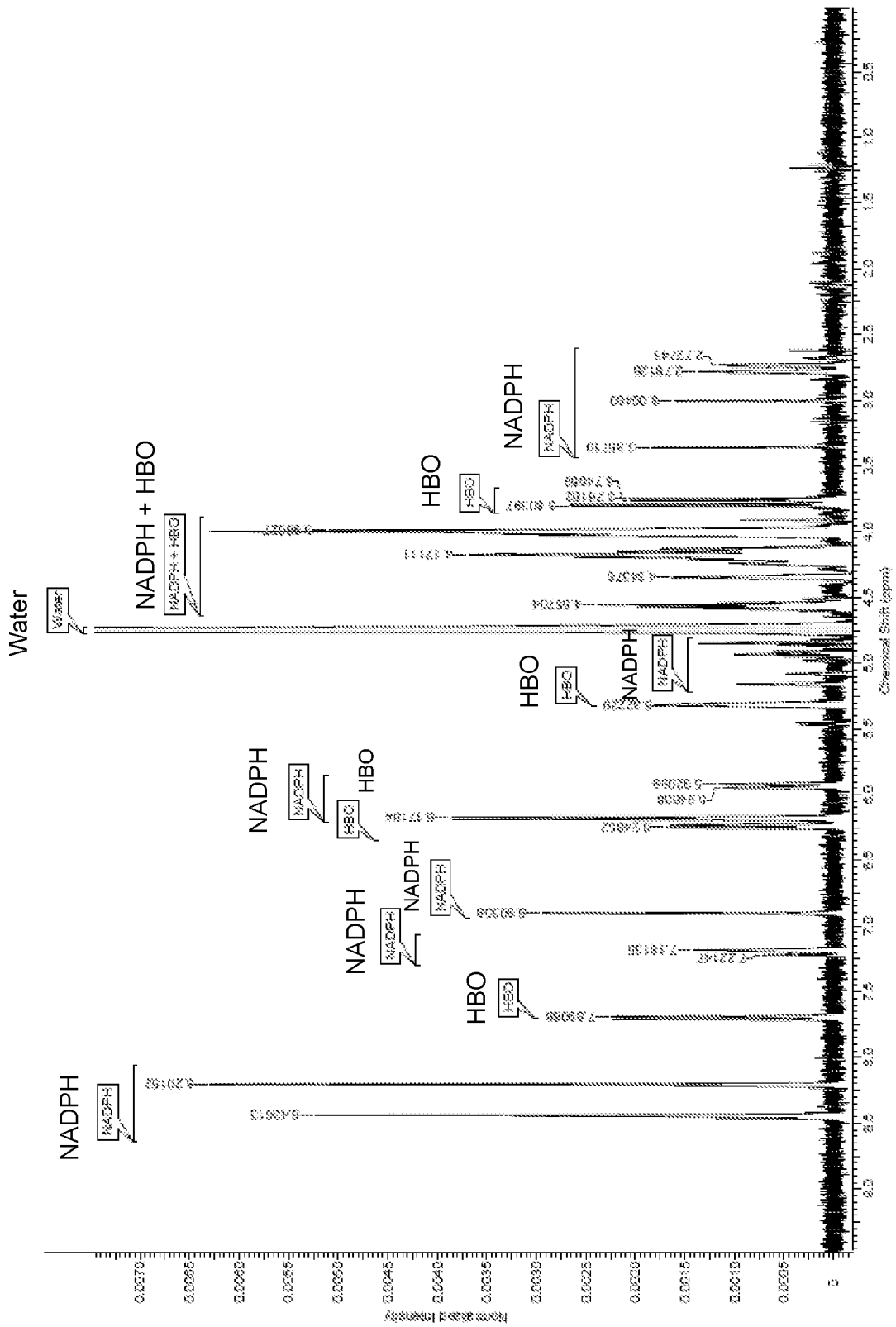
FIG. 4 shows $^1$H NMR spectrum of control reaction with (S)-γ-hydroxymethyl-α,β-butenolide (HBO).

Control reaction: $^1$H NMR (300 MHz, $CDCl_3$): δ 7.69 (1H, $H_3$), 6.25 (1H, $H_2$) (see FIG. 4).

Figure 5:
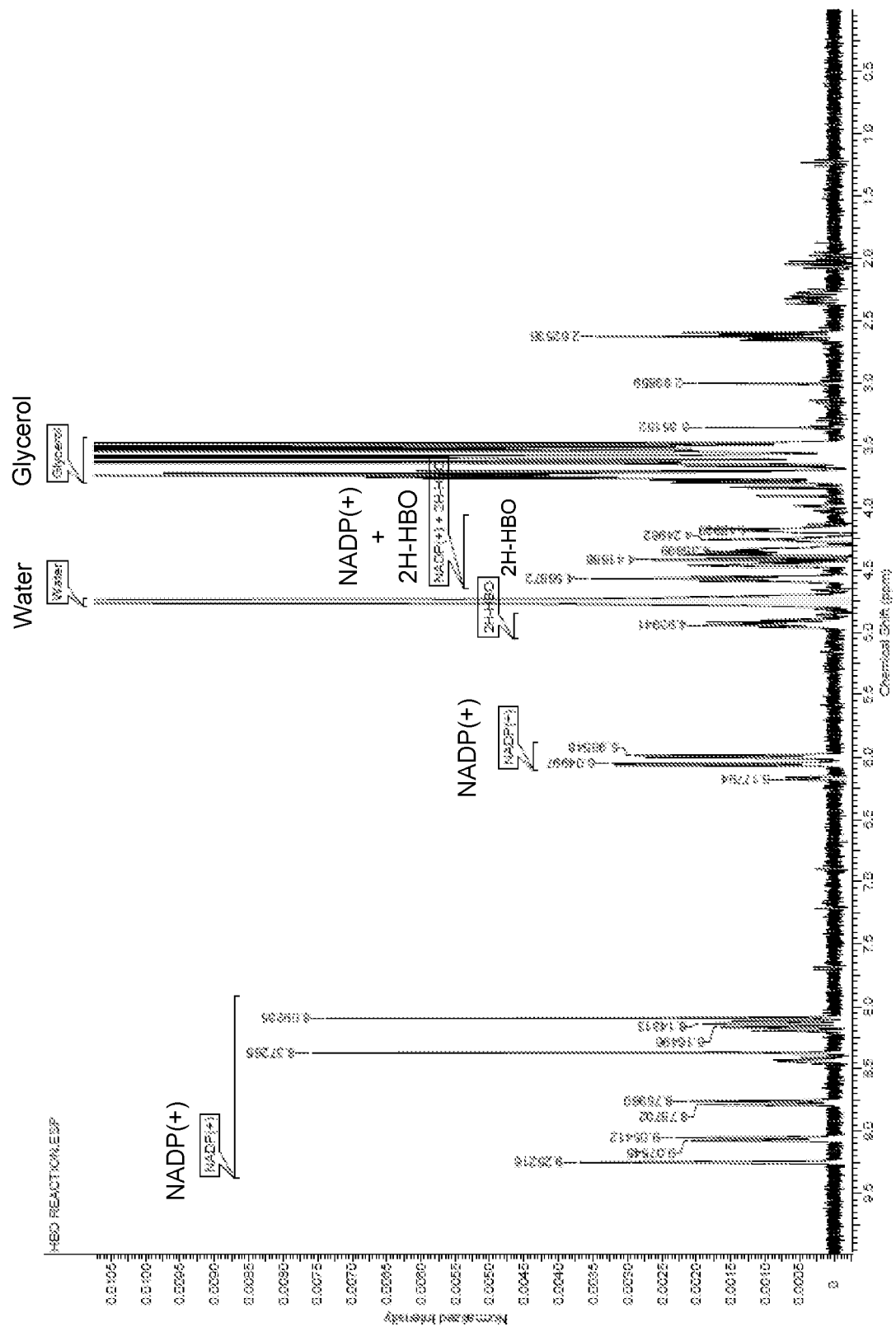
FIG. 5 shows $^1$H NMR spectrum of crude reaction: (S)-γ-hydroxymethyl-α,β-butyrolactone (2H-HBO).

Crude reaction: $^1$H NMR (300 MHz, $CDCl_3$): δ no peak for either $H_2$ or $H_3$ (see FIG. 5).

All patents, patent applications, provisional applications, and publications referred to or cited herein are incorporated by reference in their entirety, including all figures and tables, to the extent they are not inconsistent with the explicit teachings of this specification.

Following are examples that illustrate procedures for practicing the invention. These examples should not be construed as limiting. All percentages are by weight and all solvent mixture proportions are by volume unless otherwise noted.

Example 1

*Pichia stipitis* OYE 2.6 was chosen for reducing levoglucosenone since the enzyme shows higher stability under process conditions than the *S. pastorianus* OYE 1 [17]. A variety of site-directed mutants of *P. stipitis* OYE 2.6 were created with the aim of altering its stereoselectivity [18]. One particular variant, Tyr 78 Trp (Y78W), showed especially interesting properties and its x-ray crystal structure was solved [18]. While the overall size of a Trp side-chain is larger than that of Tyr, the former's shape actually creates substrate binding volume in the active site. Because levoglucosenone is a relatively large substrate, we initially tested the Y78W mutant of *P. stipitis* OYE 2.6 for its reduction. When this proved successful, we also tested wild-type *P. stipitis* OYE 2.6 as a catalyst for levoglucosenone alkene reduction. The wild-type *P. stipites* OYE 2.6 also proved successful in reduction of levoglucosenone (data not shown).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Publication No. 2012/0111714
(1) Swiderska, M. A.; Stewart, J. D. "Stereoselective Enone Reductions by *Saccharomyces carlsbergensis* Old Yellow Enzyme" *J. Mol. Catal. B: Enzymatic,* 2006, 42:52-54.

(2) Chaparro-Riggers, J. F.; Rogers, T. A.; Vazquez-Figueroa, E.; Polizzi, K. M.; Bommarius, A. S. "Comparison of Three Enoate Reductases and Their Potential Use for Biotransformations" *Adv. Synth. Catal.,* 2007, 349:1521-1531.
(3) Hall, M.; Stueckler, C.; Kroutil, W.; Macheroux, P.; Faber, K. "Asymmetric Bioreduction of Activated Alkenes Using Cloned 12-Oxophytodienoate Reductase Isoenzymes OPR-1 and OPR-3 from *Lycopersicon esculentum* (Tomato): A Striking Change of Stereoselectivity" *Angew. Chem. Int. Ed.,* 2007, 46:3934-3937.
(4) Stueckler, C.; Hall, M.; Ehammer, H.; Pointner, E.; Kroutil, W.; Macheroux, P.; Faber, K. "Stereocomplementary Bioreduction of α,β-Unsaturated Dicarboxylic Acids and Dimethyl Esters using Enoate Reductases: Enzyme- and Substrate-Based Stereocontrol" *Org. Lett.,* 2007, 9:5409-5411.
(5) Stuermer, R.; Hauer, B.; Hall, M.; Faber, K. "Asymmetric Bioreduction of Activated C=C Bonds Using Enoate Reductases from the Old Yellow Enzyme Family" *Curr. Opinion Chem. Biol.,* 2007, 11:203-213.
(6) Hall, M.; Stueckler, C.; Ehammer, H.; Pointner, E.; Oberdorfer, G.; Gruber, K.; Hauer, B.; Stuermer, R.; Kroutil, W.; Macheroux, P.; Faber, K. "Asymmetric Bioreduction of C=C Bonds Using Enoate Reductases OPR1, OPR3 and YqjM: Enzyme-Based Stereocontrol" *Adv. Synth. Catal.,* 2008, 350:411-418.
(7) Hall, M.; Stueckler, C.; Hauer, B.; Stuermer, R.; Friedrich, T.; Breuer, M.; Kroutil, W.; Faber, K. "Asymmetric Bioreduction of Activated C=C Bonds Using *Zymomobilis mobilis* NCR Enoate Reductase and Old Yellow Enzymes OYE 1-3 from Yeasts" *Eur. J. Org. Chem.,* 2008:1511-1516.
(8) Kosjek, B.; Fleitz, F. J.; Dormer, P. G.; Kuethe, J. T.; Devine, P. N. "Asymmetric Bioreduction of α,β-Unsaturated Nitriles and Ketones" *Tetrahedron: Asymmetry,* 2008, 19:1403-1406.
(9) Schweiger, P.; Gross, H.; Wesener, S.; Deppenmeier, U. "Vinyl Ketone Reduction by Three Distinct *Gluconobacter oxydans* 621H Enzymes" *Appl. Microbiol. Biotechnol.,* 2008, 80:995-1006.
(10) Adalbjornsson, B. V.; Toogood, H.; Fryszkowska, A.; Pudney, C. R.; Jowitt, T. A.; Leys, D.; Scrutton, N. S. "Biocatalysis with Thermostable Enzymes: Structure and Properties of a Thermophilic 'ene'-Reductase Related to Old Yellow Enzyme" *ChemBioChem,* 2010, 11: 197-207.
(11) Bougioukou, D. J.; Kille, S.; Taglieber, A.; Reetz, M. T. "Directed Evolution of an Enantioselective Enoate-Reductase: Testing the Utility of Iterative Saturation Mutagenesis" *Adv. Synth. Catal.,* 2009, 351:3287-3305.
(12) Burda, E.; Krauβer, M.; Fischer, G.; Hummel, W.; Müller-Uri, F.; Kreis, W.; Gröger, H. "Recombinant $\Delta^{4,5}$-Steroid 5β-Reductases as Biocatalysts for the Reduction of Activated C=C-Double Bonds in Monocyclic and Acyclic Molecules" *Adv. Synth. Catal.,* 2009, 351:2787-2790.
(13) Hirata, T.; Matsushima, A.; Sato, Y.; Iwasaki, T.; Nomura, H.; Watanabe, T.; Toyoda, S.; Izumi, S. "Stereospecific Hydrogenation of the C=C Double Bond of Enones by *Escherichia coli* Overexpressing an Enone Reductase of *Nicotiana tabacum*" *J. Mol. Catal. B: Enzymatic,* 2009, 59:158-162.
(14) Winkler, C. K.; Tasnádi, G.; Clay, D.; Hall, M.; Faber, K. Asymmetric Bioreduction of Activated Alkenes to Industrially Relevant Optically Active Compounds" *J. Biotechnol.,* 2012, 162:381-389.
(15) Formerly known as *Saccharomyces carlsbergensis*.
(16) Vaz, A. D. N.; Chakraborty, S.; Massey, V. "Old Yellow Enzyme: Aromatization of Cyclic Enones and the Mechanism of a Novel Dismutation Reaction" *Biochemistry,* 1995, 34:4246-4256.
(17) Bougioukou, D. J.; Walton, A. Z.; Stewart, J. D. "Toward Preparative-Scale, Biocatalytic Alkene Reductions" *Chem. Commun.,* 2010, 46:8558-8560.
(18) Walton, A. Z.; Sullivan, B.; Patterson-Orazem, A. "Residues Controlling Facial Selectivity in an Alkene Reductase and Semi-Rational Alterations to Create Stereocomplementary Variants" *ACS Catalysis,* 2014, 4:2307-2318.
(19) Altschul, S. F. et al. (1990) "Basic Local Alignment Search Tool" *J. Mol. Biol.* 215:402-410.
(20) Altschul, S. F. et al. (1997) "Gapped BLAST and PSI-BLAST: A New Generation of Protein Database Search Programs" *Nucl. Acids Res.* 25:3389-3402.
(21) Karlin S. and Altschul, S. F. (1990) "Methods for Assessing the Statistical Significance of Molecular Sequence Features by Using General Scoring Schemes" *Proc. Natl. Acad. Sci. USA* 87:2264-2268.
(22) Karlin S. and Altschul, S. F. (1993) "Applications and Statistics for Multiple High-Scoring Segments in Molecular Sequences" *Proc. Natl. Acad. Sci. USA* 90:5873-5877.

We claim:

1. A method for preparing 2,3-dihydro-levoglucosenone (2H-LGO), the method comprising contacting levoglucosenone (LGO) in solution with an effective amount of an Old Yellow Enzyme (OYE) in a reaction solution for a sufficient period of time to produce 2H-LGO, wherein the OYE comprises the amino acid sequence of SEQ ID NO: 1, SEQ ID NO: 2, an amino acid sequence having greater than 95% sequence identify with SEQ ID NO: 1, or an amino acid sequence having greater than 95% sequence identify with SEQ ID NO: 2.

2. The method according to claim 1, wherein the OYE is OYE 2.6 from *Pichia stipites*.

3. The method according to claim 1, wherein the solution is an aqueous solution.

4. The method according to claim 1, wherein the reaction solution comprises one or more of glucose, potassium phosphate, $NADP^+$, and glucose dehydrogenase.

5. The method according to claim 1, wherein the LGO is dissolved in ethanol.

6. The method according to claim 1, wherein the LGO is added dropwise to the reaction solution over the course of several hours.

7. The method according to claim 6, wherein the LGO is added over the course of about six hours.

8. The method according to claim 1, wherein the method further comprises purifying 2H-LGO from the solution.

9. A method for preparing (S)-γ-hydroxymethyl-α,β-butyrolactone (2H-HBO), the method comprising contacting (S)-γ-hydroxymethyl-α,β-butenolide (HBO) in solution with an effective amount of an Old Yellow Enzyme (OYE) for a sufficient period of time to produce 2H-HBO, wherein the OYE comprises the amino acid sequence of SEQ ID NO: 1, SEQ ID NO: 2, an amino acid sequence having greater than 95% sequence identify with SEQ ID NO: 1, or an amino acid sequence having greater than 95% sequence identify with SEQ ID NO: 2.

10. The method according to claim 9, wherein the OYE is OYE 2.6 from *Pichia stipitis*.

11. The method according to claim 9, wherein the solution is an aqueous solution.

12. The method according to claim 9, wherein the solution comprises one or more of potassium phosphate and NADP+.

13. The method according to claim 9, wherein the method further comprises purifying 2H-HBO from the solution.

14. The method according to claim 1, wherein the OYE is from *Saccharomyces* or *Pichia*.

15. A method for preparing 2,3-dihydro-levoglucosenone (2H-LGO), the method comprising contacting levoglucosenone (LGO) in solution with an effective amount of an Old Yellow Enzyme (OYE) in a reaction solution for a sufficient period of time to produce 2H-LGO, wherein the OYE comprises the amino acid sequence of SEQ ID NO: 1 or SEQ ID NO: 2.

16. A method for preparing (S)-γ-hydroxymethyl-α,β-butyrolactone (2H-HBO), the method comprising contacting (S)-γ-hydroxymethyl-α,β-butenolide (HBO) in solution with an effective amount of an Old Yellow Enzyme (OYE) for a sufficient period of time to produce 2H-HBO, wherein the OYE comprises the amino acid sequence of SEQ ID NO: 1 or SEQ ID NO: 2.

\* \* \* \* \*

SEQUENCE LISTING

```
<160> NUMBER OF SEQ ID NOS: 2

<210> SEQ ID NO 1
<211> LENGTH: 407
<212> TYPE: PRT
<213> ORGANISM: Pichia stipitis

<400> SEQUENCE: 1

Met Ser Ser Val Lys Ile Ser Pro Leu Lys Asp Ser Glu Ala Phe Gln
1               5                   10                  15

Ser Ile Lys Val Gly Asn Asn Thr Leu Gln Thr Lys Ile Val Tyr Pro
            20                  25                  30

Pro Thr Thr Arg Phe Arg Ala Leu Glu Asp His Thr Pro Ser Asp Leu
        35                  40                  45

Gln Leu Gln Tyr Tyr Gly Asp Arg Ser Thr Phe Pro Gly Thr Leu Leu
    50                  55                  60
```

```
Ile Thr Glu Ala Thr Phe Val Ser Pro Gln Ala Ser Gly Tyr Glu Gly
 65                  70                  75                  80

Ala Ala Pro Gly Ile Trp Thr Asp Lys His Ala Lys Ala Trp Lys Val
                 85                  90                  95

Ile Thr Asp Lys Val His Ala Asn Gly Ser Phe Val Ser Thr Gln Leu
                100                 105                 110

Ile Phe Leu Gly Arg Val Ala Asp Pro Ala Val Met Lys Thr Arg Gly
            115                 120                 125

Leu Asn Pro Val Ser Ala Ser Ala Thr Tyr Glu Ser Asp Ala Ala Lys
130                 135                 140

Glu Ala Glu Ala Val Gly Asn Pro Val Arg Ala Leu Thr Thr Gln
145                 150                 155                 160

Glu Val Lys Asp Leu Val Tyr Glu Ala Tyr Thr Asn Ala Ala Gln Lys
                165                 170                 175

Ala Met Asp Ala Gly Phe Asp Tyr Ile Glu Leu His Ala Ala His Gly
            180                 185                 190

Tyr Leu Leu Asp Gln Phe Leu Gln Pro Cys Thr Asn Gln Arg Thr Asp
            195                 200                 205

Glu Tyr Gly Gly Ser Ile Glu Asn Arg Ala Arg Leu Ile Leu Glu Leu
210                 215                 220

Ile Asp His Leu Ser Thr Ile Val Gly Ala Asp Lys Ile Gly Ile Arg
225                 230                 235                 240

Ile Ser Pro Trp Ala Thr Phe Gln Asn Met Lys Ala His Lys Asp Thr
                245                 250                 255

Val His Pro Leu Thr Thr Phe Ser Tyr Leu Val His Glu Leu Gln Gln
            260                 265                 270

Arg Ala Asp Lys Gly Gln Gly Ile Ala Tyr Ile Ser Val Val Glu Pro
            275                 280                 285

Arg Val Ser Gly Asn Val Asp Val Ser Glu Glu Asp Gln Ala Gly Asp
290                 295                 300

Asn Glu Phe Val Ser Lys Ile Trp Lys Gly Val Ile Leu Lys Ala Gly
305                 310                 315                 320

Asn Tyr Ser Tyr Asp Ala Pro Glu Phe Lys Thr Leu Lys Glu Asp Ile
                325                 330                 335

Ala Asp Lys Arg Thr Leu Val Gly Phe Ser Arg Tyr Phe Thr Ser Asn
            340                 345                 350

Pro Asn Leu Val Trp Lys Leu Arg Asp Gly Ile Asp Leu Val Pro Tyr
            355                 360                 365

Asp Arg Asn Thr Phe Tyr Ser Asp Asn Asn Tyr Gly Tyr Asn Thr Phe
            370                 375                 380

Ser Met Asp Ser Glu Glu Val Asp Lys Glu Leu Glu Ile Lys Arg Val
385                 390                 395                 400

Pro Ser Ala Ile Glu Ala Leu
                405

<210> SEQ ID NO 2
<211> LENGTH: 407
<212> TYPE: PRT
<213> ORGANISM: Pichia stipitis

<400> SEQUENCE: 2

Met Ser Ser Val Lys Ile Ser Pro Leu Lys Asp Ser Glu Ala Phe Gln
 1               5                  10                  15

Ser Ile Lys Val Gly Asn Asn Thr Leu Gln Thr Lys Ile Val Tyr Pro
```

-continued

```
                    20                  25                  30
Pro Thr Thr Arg Phe Arg Ala Leu Glu Asp His Thr Pro Ser Asp Leu
            35                  40                  45

Gln Leu Gln Tyr Tyr Gly Asp Arg Ser Thr Phe Pro Gly Thr Leu Leu
        50                  55                  60

Ile Thr Glu Ala Thr Phe Val Ser Pro Gln Ala Ser Gly Trp Glu Gly
65                  70                  75                  80

Ala Ala Pro Gly Ile Trp Thr Asp Lys His Ala Lys Ala Trp Lys Val
                85                  90                  95

Ile Thr Asp Lys Val His Ala Asn Gly Ser Phe Val Ser Thr Gln Leu
            100                 105                 110

Ile Phe Leu Gly Arg Val Ala Asp Pro Ala Val Met Lys Thr Arg Gly
        115                 120                 125

Leu Asn Pro Val Ser Ala Ser Ala Thr Tyr Glu Ser Asp Ala Ala Lys
        130                 135                 140

Glu Ala Ala Glu Ala Val Gly Asn Pro Val Arg Ala Leu Thr Thr Gln
145                 150                 155                 160

Glu Val Lys Asp Leu Val Tyr Glu Ala Tyr Thr Asn Ala Ala Gln Lys
                165                 170                 175

Ala Met Asp Ala Gly Phe Asp Tyr Ile Glu Leu His Ala Ala His Gly
            180                 185                 190

Tyr Leu Leu Asp Gln Phe Leu Gln Pro Cys Thr Asn Gln Arg Thr Asp
        195                 200                 205

Glu Tyr Gly Gly Ser Ile Glu Asn Arg Ala Arg Leu Ile Leu Glu Leu
        210                 215                 220

Ile Asp His Leu Ser Thr Ile Val Gly Ala Asp Lys Ile Gly Ile Arg
225                 230                 235                 240

Ile Ser Pro Trp Ala Thr Phe Gln Asn Met Lys Ala His Lys Asp Thr
                245                 250                 255

Val His Pro Leu Thr Thr Phe Ser Tyr Leu Val His Glu Leu Gln Gln
            260                 265                 270

Arg Ala Asp Lys Gly Gln Gly Ile Ala Tyr Ile Ser Val Val Glu Pro
        275                 280                 285

Arg Val Ser Gly Asn Val Asp Val Ser Glu Glu Asp Gln Ala Gly Asp
        290                 295                 300

Asn Glu Phe Val Ser Lys Ile Trp Lys Gly Val Ile Leu Lys Ala Gly
305                 310                 315                 320

Asn Tyr Ser Tyr Asp Ala Pro Glu Phe Lys Thr Leu Lys Glu Asp Ile
                325                 330                 335

Ala Asp Lys Arg Thr Leu Val Gly Phe Ser Arg Tyr Phe Thr Ser Asn
            340                 345                 350

Pro Asn Leu Val Trp Lys Leu Arg Asp Gly Ile Asp Leu Val Pro Tyr
        355                 360                 365

Asp Arg Asn Thr Phe Tyr Ser Asp Asn Asn Tyr Gly Tyr Asn Thr Phe
        370                 375                 380

Ser Met Asp Ser Glu Glu Val Asp Lys Glu Leu Glu Ile Lys Arg Val
385                 390                 395                 400

Pro Ser Ala Ile Glu Ala Leu
                405
```